(12) United States Patent
Colin

(10) Patent No.: US 9,878,849 B2
(45) Date of Patent: Jan. 30, 2018

(54) DEVICE, SYSTEM AND METHOD FOR PUSHING AN OBJECT ACROSS A SURFACE BY MEANS OF A MAGNETIC CONTACT ELEMENT DRIVEN BY ANOTHER MAGNETIC ELEMENT

(71) Applicant: BioMérieux, Marcy-l'Etoile (FR)

(72) Inventor: Bruno Colin, Marcy-l'Etoile (FR)

(73) Assignee: Biomerieux, Marcy-l'Etoile (FR)

(*) Notice: Subject to any disclaimer, the term of this patent is extended or adjusted under 35 U.S.C. 154(b) by 0 days.

(21) Appl. No.: 15/032,004

(22) PCT Filed: Oct. 24, 2014

(86) PCT No.: PCT/FR2014/052719
§ 371 (c)(1),
(2) Date: Apr. 25, 2016

(87) PCT Pub. No.: WO2015/059430
PCT Pub. Date: Apr. 30, 2015

(65) Prior Publication Data
US 2016/0272432 A1 Sep. 22, 2016

(30) Foreign Application Priority Data
Oct. 25, 2013 (FR) .................................... 13 60478

(51) Int. Cl.
| B65G 19/02 | (2006.01) |
| B65G 54/02 | (2006.01) |
| G01N 35/04 | (2006.01) |
| B65G 23/18 | (2006.01) |

(52) U.S. Cl.
CPC ............. *B65G 19/02* (2013.01); *B65G 23/18* (2013.01); *B65G 54/02* (2013.01); *B65G 54/025* (2013.01); *G01N 35/04* (2013.01); *B65G 2203/0216* (2013.01); *G01N 2035/0477* (2013.01)

(58) Field of Classification Search
CPC ...... B65G 19/02; B65G 54/025; B65G 23/18; B65G 54/02; B65G 2203/0216; G01N 35/04; G01N 2035/0477
See application file for complete search history.

(56) References Cited

U.S. PATENT DOCUMENTS

| 5,366,697 | A | * | 11/1994 | Tomasso | ................ | G01N 35/04 211/77 |
| 5,720,377 | A | * | 2/1998 | Lapeus | .................... | B01L 9/06 198/346.1 |
| 6,571,934 | B1 | | 6/2003 | Thompson | | |
| 7,028,831 | B2 | * | 4/2006 | Veiner | .................... | G01N 35/04 198/465.1 |
| 2005/0207937 | A1 | * | 9/2005 | Itoh | ....................... | G01N 35/04 422/63 |

(Continued)

FOREIGN PATENT DOCUMENTS

JP 2002223926 A 8/2002

OTHER PUBLICATIONS

International Search Report and Written Opinion dated Feb. 24, 2015 for International Patent Application No. PCT/FR2014/052719.

*Primary Examiner* — Mark A Deuble
(74) *Attorney, Agent, or Firm* — Pepper Hamilton LLP

(57) ABSTRACT

A device (10) for conveying an object (60) in order to move said object (60) from an initial position to a final position, on a conveying surface (46).

19 Claims, 12 Drawing Sheets

(56) References Cited

U.S. PATENT DOCUMENTS

2009/0035185 A1* 2/2009 Tsujimura ............... B01L 9/06
    422/400
2012/0266698 A1* 10/2012 Isobe ................. G01N 35/026
    73/863.92
2012/0295358 A1 11/2012 Ariff

* cited by examiner

DEVICE, SYSTEM AND METHOD FOR PUSHING AN OBJECT ACROSS A SURFACE BY MEANS OF A MAGNETIC CONTACT ELEMENT DRIVEN BY ANOTHER MAGNETIC ELEMENT

CLAIM OF PRIORITY

This application is a U.S. national stage filing under 35 U.S.C. § 371 of International Application No. PCT/FR2014/052719, filed on Oct. 24, 2014 and entitled "DEVICE, SYSTEM AND METHOD FOR PUSHING AN OBJECT ACROSS A SURFACE BY MEANS OF A MAGNETIC CONTACT ELEMENT DRIVEN BY ANOTHER MAGNETIC ELEMENT," which claims priority from French Patent Application Number 1360478, filed on Oct. 25, 2013, both of which are incorporated herein by reference in their entirety.

TECHNICAL FIELD

The invention relates to a device, a system and a method of conveying an object, and more specifically a container suitable for containing a sample intended for being processed and/or analysed.

STATE OF THE ART

The use of conveying devices in the field of processing and biological analysis of samples is very widespread. Indeed, generally, a sample located inside an object such as a container may undergo specific processing within a processing system in order to introduce a suitable culture medium inside the container. Then the sample inside the container may need to be cultured within an incubator in order to enable the development of certain bacteria, due to the presence of the suitable culture medium. Finally, the sample within the container may also undergo analyses within an analysis system, in order to determine the nature and the type of bacteria present within the container, following incubation for example. The various processing systems, analysis systems and the incubator are not generally arranged near one another. Conveying devices are therefore provided in order to route the object successively toward the various processing and analysis systems for example. Furthermore, additional systems may prove necessary according to the type of processing and/or analysis desired for the sample concerned. Thus, the conveying devices must therefore make it possible to route the object over various distances to various devices and/or systems.

In the prior art, there are various types of conveying devices which make it possible to move objects such as sample containers.

Thus, U.S. Pat. No. 6,571,934 discloses a first type of container conveying device. The containers are located within a container support. Thus, the conveying device makes it possible to convey the container support. The contents of a container notably comprises a sample. The conveying device makes it possible to prevent spilling the contents of the containers when conveying the container support on a conveying surface. The container support is formed by an upper surface and a lower surface. The lower surface is in contact with the conveying surface and comprises a magnetic element such as a ferromagnetic element. The conveying device also comprises a transmission belt located below the conveying surface and a permanent magnet located on the surface of the transmission belt. More precisely, the permanent magnet is situated within a sealed cavity so as to be able to slide freely in the sealed receptacle, in a plane which is parallel relative to the horizontal plane of movement of the container. The ferromagnetic element and the permanent magnet are suitable for cooperating together. Thus, as the transmission belt rotates, the permanent magnet moves progressively closer to the magnetic element associated with the container support, said container support being immobile on the conveying surface. As the permanent magnet moves closer to the magnetic element, the attraction force of the permanent magnet on the magnetic element increases. When the attraction force of the permanent magnet on the magnetic element is greater than the resistance force of the container support on the conveying surface, then the container support is driven on the conveying surface. Insofar as the permanent magnet is mobile within the sealed cavity, the initial shifting movement created by the attraction force is absorbed by the permanent magnet, which then moves within the sealed cavity. The moving, or similarly the immobilising, of the container support is therefore carried out progressively, without causing an abrupt movement of the container support. Thus, any spilling of the contents of one or more containers may be prevented. Furthermore, the conveying device enables linear movement of the container support, along a defined linear track on the conveying surface, as well as an angular movement of the container support with the aid of a rotating arm, outside of the linear track.

However, the conveying device according to U.S. Pat. No. 6,571,934 necessitates having a container support suitable for a certain type of container. Thus, when a user wishes to perform analysis of a sample located within a first container not suitable for the container support designed for the conveying device, they must transfer the contents, including the sample, from the first container into a second container suitable for the container support. This transfer of contents may bring about a contamination of the contents which may harm the sterility of the contents. Moreover, this transfer stage generates an additional stage which negatively impacts on productivity.

Furthermore, the conveying device according to U.S. Pat. No. 6,571,934 necessitates having container supports comprising magnetic means and specifically adapting these magnetic means for the conveying of containers. Thus, the use of such a conveying device generates substantial costs linked to the manufacture of specific container supports intended for use with a specific conveying device.

Finally, the conveying device according to U.S. Pat. No. 6,571,934 imposes limited possibilities for container movement. Furthermore, these movements apply only to the container support, i.e. to a group of containers.

The international patent application WO 2005/093433 discloses a second type of conveying device also suitable for a container support. This conveying device comprises bidirectional driving means in order to enable the container support to move in two perpendicular directions. However, implementation of this conveying device necessitates the use of two linear driving systems, each including complex and specific driving means. This conveying device is therefore both difficult and expensive to implement.

It therefore proves necessary to enable the conveying of objects by means of a conveying device having a simple structure, suitable for any type of object and offering various possibilities for moving the object.

Furthermore, during the conveying of a container, the movement of the container may cause the container to fall and therefore cause the contents of the container to discharge onto the conveying surface. The conveying surface is then contaminated by the container contents. Depending on the nature and the structure of the conveying surface, the conveying surface is difficult to clean and disinfect.

It therefore proves necessary to provide a conveying device which makes it possible to easily clean and disinfect the conveying surface.

It also proves necessary to enable the use of a conveying device integrated within a conveying system with a simple design and which is inexpensive, while offering a substantial number of possibilities for moving the object.

Finally, it proves necessary to devise a conveying method relating to said conveying device and system.

OBJECT OF THE INVENTION

With reference to the above observations, an objective of the present invention consists in providing a device, a system and a method of conveying which makes it possible to resolve at least one of the disadvantages mentioned above.

SUMMARY OF THE INVENTION

Thus according to the first aspect of the invention, the present invention relates to a device for conveying an object in order to move said object from an initial position to a final position, on a conveying surface, said conveying device comprising:
  at least one conveying belt, i.e. a first conveying belt, which is rotationally mobile with the aid of corresponding driving means and which is located under the conveying surface, said at least one conveying belt making it possible to define a conveying path on the conveying surface;
  a magnetic driving device comprising:
    at least one first magnetic means, such as a permanently magnetised magnetic means, said first magnetic means being integral with said at least one conveying belt and moving with said conveying belt below the conveying surface;
    and at least one second magnetic means, such as a ferromagnetic means positioned on the conveying surface and suitable for moving on said conveying surface, driven by said at least one first magnetic means through the conveying surface;
  a contact device suitable for applying a contact force onto the external wall of the object,
  so that, when said at least one conveying belt is moving in the presence of an object on the conveying surface, the second magnetic means moves on the conveying surface, along the conveying path, driven by the first magnetic means, by applying a movement force onto the external wall of the object and the contact device simultaneously applies at least one contact force onto the external wall of the object to enable the guided movement of said object on the conveying surface.

Advantageously, the contact device comprises a second magnetic driving device comprising at least one first magnetic means such as a permanently magnetised magnetic means, said first magnetic means being integral with at least one second conveying belt, which is distinct from the first conveying belt, and which moves with said at least second conveying belt below the conveying surface and at least one second magnetic means such as a ferromagnetic means positioned on the conveying surface and suitable for being moved on said conveying surface driven by said at least one first magnetic means through the conveying surface.

Alternatively, the contact device comprises a guiding device positioned on the conveying surface.

Advantageously the conveying device comprises a conveying belt and the guiding device comprises a central support which is immobile on the conveying surface.

Advantageously, the conveying device comprises a first movement device including a first magnetic movement means located removably between a first conveying path and a second conveying path on the conveying surface and suitable for cooperating with a second magnetic movement means located below the conveying surface to rotate the first magnetic movement means.

Advantageously the conveying device comprises a second movement device including a first magnetic movement means located removably inside a first conveying path on the conveying surface and suitable for cooperating with a third magnetic movement means located below the conveying surface to enable free rotation of the first magnetic movement means.

Advantageously the second movement device comprises a second magnetic movement means located removably inside a second conveying path on the conveying surface and suitable for cooperating with a fourth magnetic movement means located below the conveying surface to rotate the second magnetic movement means.

Advantageously, the conveying device comprises a third movement device comprising a rotating arm located on or above the conveying surface and actuated by an angular movement of a fixed angle value for moving the object on the conveying surface.

According to the second aspect of the invention, the present invention relates to a conveying system comprising at least one conveying device mentioned above.

Advantageously the conveying system comprises a detection device such as an electro-optical sensor for detecting the position of the object on the conveying surface.

Advantageously, a control device in order to control the movement of at least one conveying belt.

Advantageously, the control device makes it possible to control the triggering of the first and/or of the second and/or of the third movement device depending on the detected position of the object on the conveying surface.

Advantageously the conveying system comprises an optical reading device for reading the content of an information medium located on the object.

According to a third aspect of the invention, the present invention relates to a conveying method for moving an object on a conveying surface from an initial position to a final position, at least one first magnetic means being arranged below the conveying surface, said at least one first magnetic means being integral with at least one conveying belt, a second magnetic means being arranged on the conveying surface and suitable for cooperating with the first magnetic means through the conveying surface and for applying a movement force onto the external wall of the object, said conveying method comprising the following stages:
  starting rotation of the conveying belt with the aid of driving means in order to enable movement of the first magnetic means;
  cooperation of the first magnetic means and the second magnetic means to enable the guided movement of said second magnetic means along a corresponding conveying path, on the conveying surface;
  application of a movement force by the second magnetic means in movement, on the external wall of the object;

application of at least one contact force onto the external wall of the object by a contact device, simultaneously with the application of the movement force to enable guided movement of the object on the conveying surface.

BRIEF DESCRIPTION OF THE DRAWINGS

The invention, its functionality, its applications and its advantages shall be better understood by reading the present description, made with reference to the figures, wherein.

DETAILED DESCRIPTION OF THE INVENTION

Figure 1:
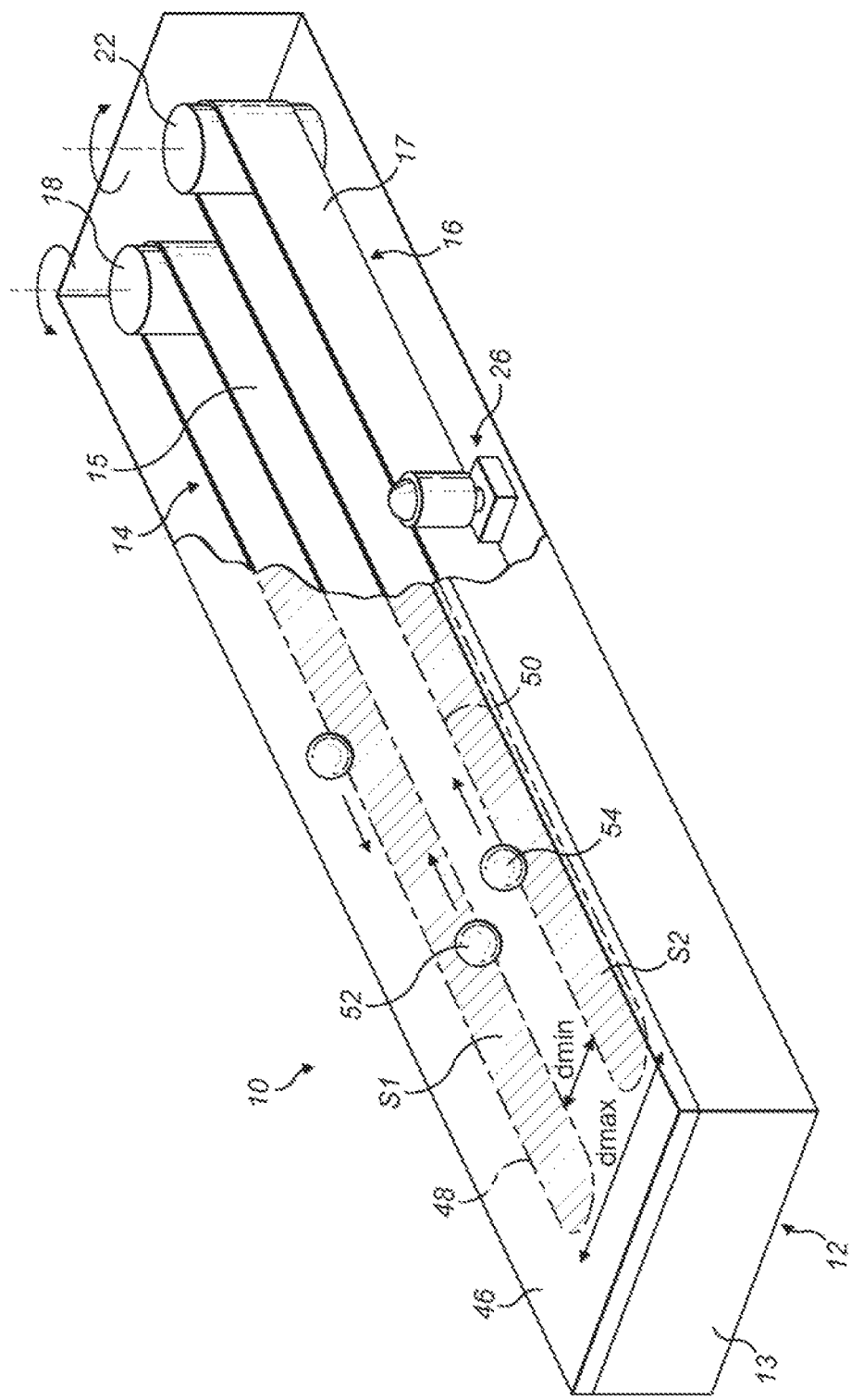
FIG. 1 shows a conveying device according to a partial exterior view and a partial interior view, and comprising two conveying belts, a magnetic driving device and a contact device, said contact device comprising a first and a second magnetic means according to one embodiment of the invention.

The detailed description below aims to set out the invention in a manner which is sufficiently clear and complete, notably by means of examples, but must by no means be regarded as limiting the scope of protection to the particular embodiments and the examples presented below.

Within the present invention, the shape and dimensions of the conveying device are suitable for the shape and dimensions of the object to be conveyed. Advantageously, the object is a container such as a Petri dish which contains contents such as a culture medium and a sample to be observed and/or analysed.

Thus, according to the present invention, the sample may be from various origins, for example of food, environmental, veterinary, clinical, pharmaceutical or cosmetic origin.

Amongst the samples of food origin, non-exhaustive mention can be made of a sample of dairy products (yogurts, cheeses, etc.), meat, fish, egg, fruit, vegetable, water, beverages (milk, fruit juice, soda, etc.). Of course, these samples of food origin can also come from sauces or more complex meals, or from unprocessed or partially processed raw materials. A sample of food origin can also come from an animal feed, such as oil cakes, animal meals.

As indicated previously, the sample can be of environmental origin and can consist, for example, of a surface specimen, water specimen, air specimen, etc.

The sample can also consist of a sample of clinical origin, which can correspond to specimens of biological fluid (urine, whole blood or derivatives such as serum, saliva, pus, cerebrospinal fluid, etc.), of stools (for example cholera-induced diarrhoea), of specimens from the nose, throat, skin, wounds, organs, tissues or isolated cells. This list is obviously not exhaustive.

Preferably, the sample is of pharmaceutical origin, and corresponds for example to pharmaceutical preparations or vaccine preparations.

Generally, the term "sample" refers to a part or a quantity, more particularly a small part or a small quantity, sampled from one or more entities for the purpose of analysis. This sample can possibly have undergone a pretreatment, involving for example mixing, dilution or even crushing stages, in particular if the starting entity is solid-state.

The sample collected is, in general, capable of—or suspected of—containing at least one target microorganism, and mainly a bacterium.

The term "microorganism" has the same meaning as that generally accepted in microbiology and comprises notably gram-positive or gram-negative bacteria, yeasts, moulds and more generally, single-cell organisms, invisible to the naked eye, which can be manipulated and multiplied in a laboratory.

Advantageously, the sample is placed in contact with at least one culture medium, enabling the growth of the microorganisms and, in particular of the target microorganism(s). "Culture medium" is to be understood to be a medium comprising all the elements necessary for the survival and/or for the growth of the microorganisms and, in particular, of the microorganisms sought (for example buffered peptone water). The culture medium may contain possible additives, for example: peptones, one or more growth factors, carbohydrates, one or more selective agents, buffers, one or more vitamins, etc.

The present invention relates to a conveying device 10 such as shown in FIG. 1. The conveying device 10 comprises a receptacle 12 equipped with a wall 13. The height of the wall 13 may be from 15 to 20 cm. The receptacle 12 contains one conveying belt and preferably two conveying belts 14, 16 such as transmission belts.

Figure 2:
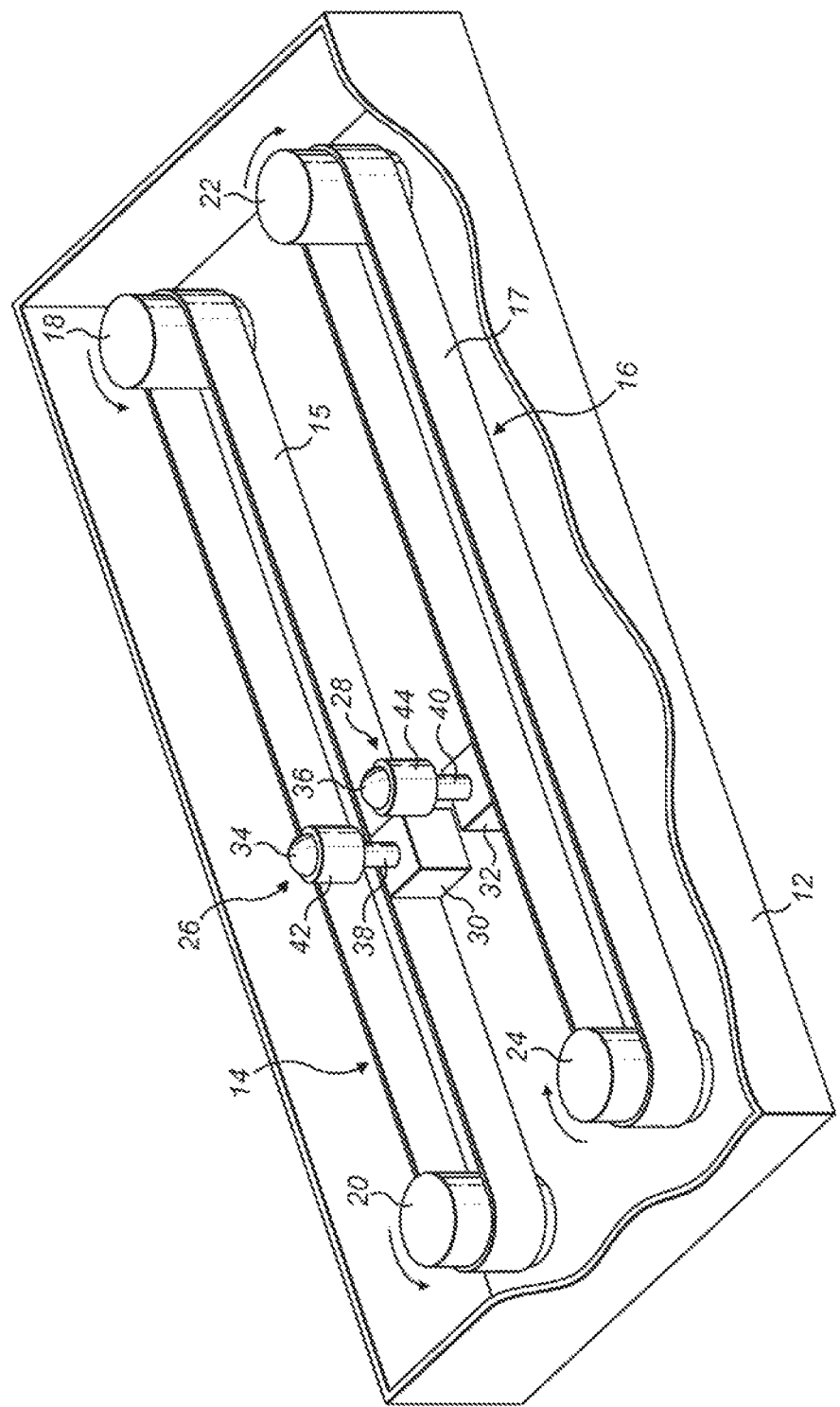
FIG. 2 shows an interior view of a conveying device according to FIG. 1, each conveying belt including a first magnetic means according to one embodiment of the invention.

The conveying belt 14 has a belt surface 15 and is driven by two driving means 18, 20 as shown in FIG. 2. The conveying belt 16 has a surface 17 and is driven by two driving means 22, 24 as shown in FIG. 2. The surfaces 15, 17 designated below as the belt surfaces 15, 17, are arranged in a plane perpendicular to the horizontal plane of the receptacle 12.

As shown in FIG. 1, the belt surfaces 15, 17 possess a minimum spacing distance dmin and a maximum spacing distance dmax.

The minimum spacing distance dmin corresponds to the minimum distance between a portion of the belt surface 15 and a portion of the belt surface 17, i.e. when the portions of the belt surfaces 15, 17 concerned are located in a central zone inside the receptacle 12 away from the wall 13 of said receptacle 12.

The maximum spacing distance dmax corresponds to the maximum distance between a portion of the belt surface 15 and a portion of the belt surface 17, i.e. when the portions of the belt surfaces 15, 17 concerned are located in an interior zone of the receptacle 12 and close to the wall 13 of said receptacle 12.

The driving means 18, 20, 22, 24 comprise any type of suitable means such as a cylindrical post powered by an electrical motor, such as a stepper motor. The driving means 18, 20 drive the conveying belt 14 in a first rotation direction. The driving means 22, 24 drive the conveying belt 16 in a second rotation direction, opposite to the first direction of rotation. The conveying belts 14, 16 describe an ellipsoidal or circular rotation, for example. Thus, the conveying belts 14 and 16 move such that, when a portion of the belt surface 15 and a portion of the belt surface 17 arranged at a minimum spacing distance dmin are considered, said belt surfaces 15, 17 move in the same direction relative to one another. The movement direction of the belt surfaces 15, 17 in the central zone of the receptacle 12 and away from the wall 13 is therefore opposite to the movement direction of the belt surfaces 15, 17 in the peripheral zone of the receptacle 12 situated close to the wall 13 of the receptacle 12.

According to a preferred embodiment, the conveying device 10 comprises a first magnetic driving device and a contact device constituted by a second magnetic driving device. The first and second magnetic driving devices are described below.

As shown in FIG. 2, the first magnetic driving devices 26, 28 are each associated with a conveying belt 14, 16.

As shown in FIGS. 1 and 2, according to the preferred embodiment, the magnetic driving devices each comprise a first magnetic means 26, 28 and a second magnetic means 52, 54 suitable for cooperating with the first magnetic means 26, 28.

As shown in FIG. 2, the first and second magnetic driving devices comprise the first magnetic means 26, 28 fixed to the conveying belt 14, 16. The first magnetic means 26, 28 comprise a retaining post 30, 32 fixed onto the belt surface 15, 17. The fixing may be carried out by means of any type of fixture, such as an element made of adhesive material or a mechanical fixture such as a screw. The first magnetic means 26, 28 comprise a permanent magnet 34, 36. The permanent magnet 34, 36 is made from an alloy comprising neodymium, samarium or any other rare earth metal, as well as iron, boron and cobalt for example. The permanent magnet 34, 36 is ball-shaped. Alternatively, the permanent magnet 34, 36 may take the form of a cylindrical post, for example. The permanent magnet 34, 36 is linked to the retaining post 30, 32 by a retaining rod 38, 40 which corresponds to the vertical central axis of the retaining post 30, 32. The retaining rod 38, 40 is joined between the permanent magnet 34, 36 and the retaining post 30, 32 by means of a mechanical element which has elastic properties, such as a spring. Thus, the permanent magnet 34, 36 may be fixed to the retaining post 30, 32 while guaranteeing the permanent magnet 34, 36 freedom of movement. According to a preferred embodiment, the permanent magnet 34, 36 is located within a magnet support 42, 44 in order to guarantee the permanent magnet 34, 36 a stable position. The magnet support 42, 44 comprises a suitable cavity in order to receive the permanent magnet 34, 36. The magnet support 42, 44 is fixed to the retaining post 30, 32 in order to enable freedom of movement of the magnet support 42, 44 and therefore freedom of movement of the permanent magnet 34, 36 associated with the movement of the magnet support 42, 44.

Thus, when the conveying belt 14, 16 moves, the retaining post 30, 32 moves simultaneously in the same rotation direction as that of the conveying belt 14, 16. Consequently, the permanent magnet 34, 36 moves simultaneously with the corresponding retaining post 30, 32.

In a preferred initial position, the first magnetic means 26, 28 are arranged symmetrically on the belt surfaces 15, 17. Thus, the first magnetic means 26, 28 and the second magnetic means 52, 54 are moved synchronously.

Each permanent magnet 34, 36 may be situated away from or in contact with the conveying surface 46. Preferably, each permanent magnet 34, 36 is situated at a fixed distance from the conveying surface 46 in order to prevent the presence of friction forces between each permanent magnet 34, 36 and the conveying surface 46 during the movement of the first magnetic means 26, 28. Thus, the production of noise disturbances caused by these friction forces is prevented. The determination of the distance between each permanent magnet 34, 36 and the conveying surface 46 depends on the desired magnetic coupling between the first magnetic means 26, 28 and the second magnetic means described below.

As shown in FIG. 1, the conveying device 10 also comprises a conveying plane 46. The conveying plane 46 is made of an insulating material comprising a substantially smooth surface, such as glass, stainless steel, laminate wood or copper. The thickness of the conveying plane 46 is relatively small, in the order of a few millimetres (mm) and generally less than 10 mm. Alternatively, the conveying plane 46 may be made of an insulating material comprising a substantially rough surface. Thus, when an object moves on the conveying plane 46, the movement speed of said object may be controlled in line with the quality of the roughness of said conveying plane 46. Isolated accelerations of the object may then be reduced when said object collides with other objects arranged on the conveying plane 46. Given the small thickness of the conveying plane 46, in the remainder of the description, the conveying plane 46 is likened to a conveying surface 46.

The conveying surface 46 is suitable for resting on the walls 13 of the receptacle 12 in order to cover the conveying belts 14, 16, the driving means 18, 20, 22, 24 and the first magnetic means 26, 28 shown in FIG. 2.

As shown in FIG. 1, the conveying surface 46 comprises two conveying paths 48, 50 respectively associated with the location of the conveying belts 14, 16 located below the conveying surface 46.

The belt surface 15, 17 delimits an inner volume situated below the conveying surface 46 which corresponds to a surface delimitation on the conveying surface 46. Thus, the surface delimitation of the belt 15 corresponds to a first inner surface S1 on the conveying surface 46 and to a second inner surface S2 on the conveying surface 46. The first and second inner surfaces S1 and S2 occupy the same area.

According to the preferred embodiment described above, the two magnetic driving devices each comprise a second magnetic means 52, 54 designed to cooperate with the first magnetic means 26, 28. The second magnetic means 52, 54 are positioned on the outlines of the inner surfaces S1 and S2 on the conveying surface 46.

Figure 3:
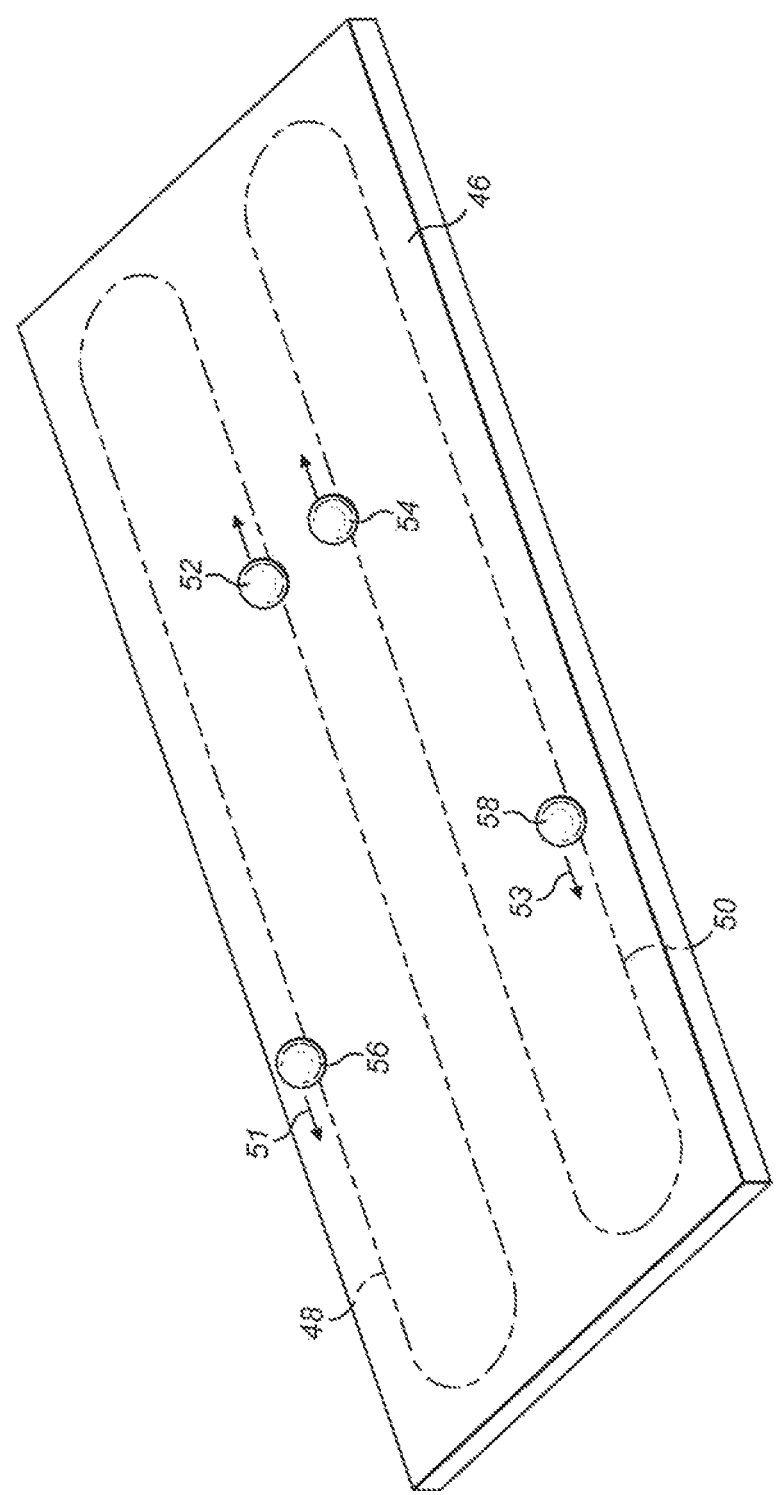
FIG. 3 shows a conveying surface of the conveying device according to FIG. 1, a plurality of second magnetic means being located on the conveying surface according to one embodiment of the invention.

As shown in FIG. 3 the second magnetic means 52, 54 are suitable for being moved on a conveying path 48, 50 in the direction of the movement arrows 51, 53. The movement of the second magnetic means 52, 54 is synchronous such that, for a pair of second magnetic means 52, 54, one second magnetic means 52 is located symmetrically on the conveying path 48 relative to the other second magnetic means 54 on the conveying path 50. According to a preferred initial position, the second magnetic means 52, 54 are located above the first magnetic means 26, 28. Thus, the second magnetic means 52, 54 are moved when the belts 14, 16 are moved. Alternatively, if the initial position of the second magnetic means 52, 54 does not correspond to the preferred initial position described above, the second magnetic means 52, 54 are simultaneously moved only when the first magnetic means 26, 28, moved by the belts 14, 16, are at a relatively small fixed distance from the second magnetic means 52, 54 which is defined according to specific conditions. These specific conditions require that the respective attraction force of the first magnetic means 26, 28 on the respective second magnetic means 52, 54 is greater than the sum of the forces applied to the second magnetic means 52, 54 taking into consideration the thickness of the conveying surface 46. This sum of forces comprises, firstly, the resistance force of the second magnetic means 52, 54 relative to the conveying surface 46. The resistance force depends on the material and the regularity of the conveying surface 46. The sum of forces comprises, secondly, the gravity force of the second magnetic means 52, 54. Thus, the second magnetic means 52, 54 are made of a ferromagnetic material or of a material enabling permanent magnetisation. The second magnetic means 52, 54 may take the form of a ball, a ball bearing or a cylindrical post, for example. If the second magnetic means 52, 54 each have the form of a cylindrical post, a ferromagnetic material may be inserted inside said cylindrical post in order to obtain a magnetic coupling with the first magnetic means 26, 28 arranged below the conveying surface 46. The cylindrical post may preferably comprise a minimum contact surface with the conveying surface 46. Thus, during a period of immobilisation, in the order of several hours, of the cylindrical post, the presence of adhesion forces between the cylindrical post and the conveying surface 46 may be minimised. The cylindrical post may therefore comprise, for example, three distinct supports in contact with the conveying surface 46. Thus, when said second magnetic means 52, 54 in the form of a cylindrical post are moved after a distinct prolonged stoppage period, said second magnetic means 52, 54 move regularly, without jerking. The second magnetic means 52, 54 therefore each constitute a removable element which may be easily removed from the conveying surface 46 in order to be disinfected, cleaned, or replaced and also in order to clean, disinfect or replace the conveying surface 46, for example.

The dimensions and the material of the second magnetic means 52, 54 depend on the dimensions and the material of the first magnetic means 26, 28. According to the present invention, a magnetic coupling, through the conveying surface 46, between the first magnetic means 26, 28 and the second magnetic means 52, 54 is necessary. Indeed, with a fixed magnetic coupling, starting rotating of the conveying belt 14, 16 moves the second magnetic means on the conveying surface 46. Thus, the dimensions and the material of the second magnetic means 52, 54 are suitable to make it possible to obtain a fixed magnetic coupling between the first magnetic means 26, 28 and the second magnetic means 52, 54.

Figure 4:
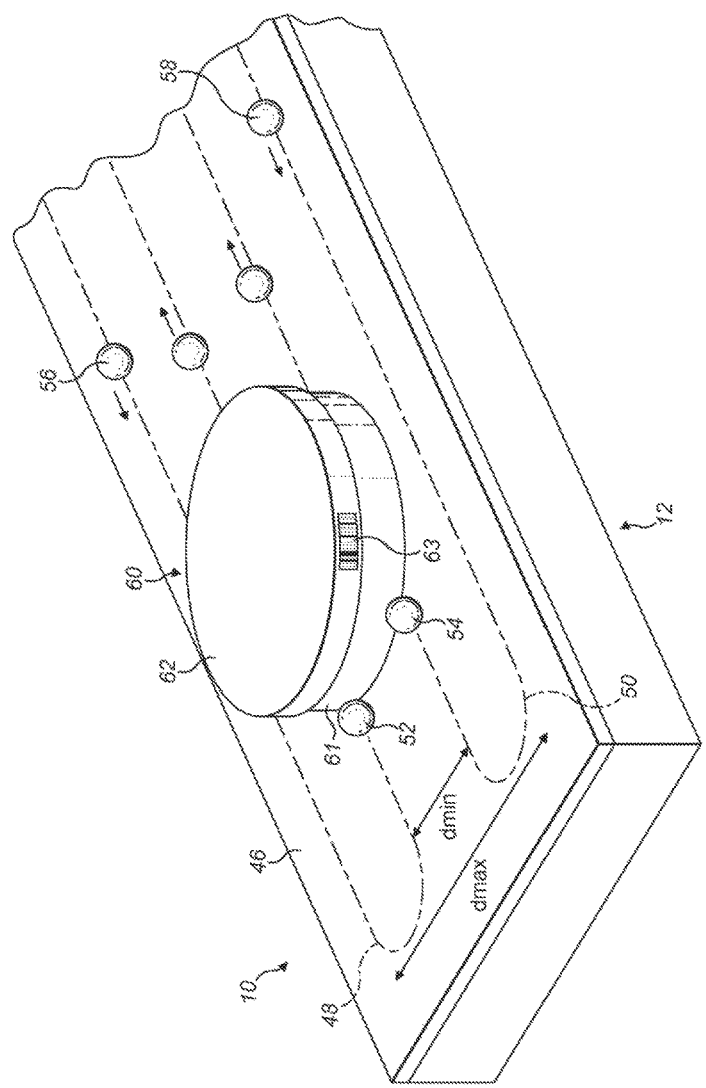
FIG. 4 shows a detailed view of a conveying device according to FIGS. 1, 2 and 3 in the presence of second magnetic means according to one embodiment of the invention.

Thus, in the presence of a strong magnetic coupling, when the second magnetic means 52, 54 are moving on a conveying path 48, 50 and come into contact with an obstacle or an object such as a Petri dish 60 depicted in FIG. 4, then the second magnetic means 52, 54 are not deflected from the conveying path 48, 50.

Alternatively, in the presence of a weak magnetic coupling, when the second magnetic means 52, 54 are displaced on a corresponding conveying path 48, 50 and come into contact with an obstacle or an object such as a Petri dish 60, then the second magnetic means 52, 54 are suitably deflected from the conveying path 48, 50. Thus, the second magnetic means 52, 54 may undergo a movement which corresponds to a separation according to a separation zone defined relative to the corresponding conveying path 48, 50, while preserving the effect of the magnetic coupling between the first magnetic means 26, 28 and the second magnetic means 52, 54. This separation makes it possible for the second magnetic means 52, 54 to remain in contact with the conveying path 48, 50 and to continue to drive and guide the Petri dish 60 on the conveying surface 46.

The magnetic coupling may therefore be modulated by adapting the dimensions and the materials of the first magnetic means 26, 28 to the dimensions and the materials of the second magnetic means 52, 54. Thus, depending on the type of magnetic coupling, the second magnetic means 52, 54 have a fixed separation zone relative to the respective conveying paths 48, 50 when the conveying belts 14, 16 start rotating.

As shown in FIG. 3, additional second magnetic means 56, 58 may be arranged on the conveying surface 46 if additional first magnetic means (not visible) are arranged on the conveying belts 14, 16. The additional second magnetic means 56, 58 are arranged on the respective conveying paths 48, 50 according to the initial position described above. The second magnetic means 52, 54, 56 and 58 operate in pairs. The additional second magnetic means 56 is moved synchronously with the additional second magnetic means 58. The additional second magnetic means 56, 58 being respectively moved by the additional first magnetic means (not visible).

The additional second magnetic means 56, 58 may be arranged on the conveying surface 46 in a fixed manner, so that when the Petri dish 60 is present, the second magnetic means 52, 54 and the additional second magnetic means 56, 58 are all in contact with said Petri dish 60. Thus, the Petri dish 60 may be guided optimally on the conveying surface 46. Alternatively, the additional second magnetic means 56, 58 may be arranged on the conveying surface 46 in order to guide a second Petri dish (not shown).

As shown in FIG. 4, the conveying surface 46 has the function of making it possible to convey a Petri dish 60. The Petri dish 60 may comprise a receptacle 61 and a lid 62. The lid 62 may also comprise an information medium 63 in particular enabling identification of the type of object and/or the nature of the contents of the Petri dish 60, for example. The information medium 63 may be a label equipped with a barcode in order to enable subsequent reading of the barcode by an optical reading device, for example. A fixed surface or contact surface of the Petri dish 60, of fixed dimension is in contact with the conveying surface 46. The Petri dish 60 may initially be arranged on the conveying surface 46 such that the receptacle 61 is in contact with the conveying surface 46. Alternatively, the Petri dish 60 may initially be arranged on the conveying surface 46 such that the lid 62 is in contact with the conveying surface 46. The Petri dish 60 comprises a wall which is also referred to in the present description as the external wall or lateral external wall of the Petri dish 60. The lateral external wall of the Petri dish 60 comprises the lateral external wall of the receptacle 61 and the lateral external wall of the lid 62. The Petri dish 60 may be placed in any initial position whatsoever. Preferably, the Petri dish 60 is placed at a fixed initial position, for example at one end of the conveying surface 46.

The shape and the dimension of the various elements of the conveying device 10, such as the conveying belts, the first and the second magnetic means, must be suitable for the shape and dimensions of the Petri dish 60, in particular for the shape and the dimensions of the contact surface. The dimensions of the conveying device 10 are defined such that when the Petri dish 60 is in the initial position, the contact surface of the Petri dish 60 is in a zone delimited by the distances dmin and dmax associated with the belt surfaces 15, 16. Preferably, in an initial position, the Petri dish 60 is arranged centrally between the two conveying paths 48, 50, as shown in FIG. 4. The Petri dish 60 may be routed manually, or automatically by means of a suitable feeding device (not visible), as far as the initial position on the conveying surface 46.

Preferably, concerning the Petri dish 60, the value of the diameter of the contact surface of the Petri dish 60 may be between 60 and 100 mm. Advantageously, the value of the diameter is between 60 and 90 mm. The values of the dimensions dmin and dmax between the belt surfaces 15, 17 are suitable so that the value of the diameter of the Petri dish 60, in its initial position, is greater than the dmin value and lower than the dmax value.

Optionally, the value of the diameter of the contact surface of the Petri dish 60 may be greater than 100 mm. Indeed, a layer of absorbent material may be applied onto the circumference of said contact surface of the Petri dish. The presence of the absorbent material makes it possible to absorb the impacts generated when the second magnetic means 52, 54 come into contact with the Petri dish 60, notably when said second magnetic means 52, 54 strike said Petri dish 60 stationary on the conveying surface 46.

The Petri dish 60 contains, for example, a sample intended to undergo processing and/or an analysis. Indeed, the sample may, for example, have already been subjected to culturing by means of a culture medium suitable for enabling the development of specific bacteria. Thus, the sample requires incubation within an incubator in order to put the sample into conditions which are favourable to the development of bacteria. This incubation necessitates conveying the Petri dish 60 up to said incubator (not visible).

The Petri dish 60 may also be conveyed specifically to a particular destination such as a storing zone, a reject zone or a specific analysis system.

Thus, various possibilities for conveying or routing the Petri dish 60 may prove necessary depending on the user's needs.

During the operation of the conveying device according to the invention, the Petri dish 60 is arranged on the conveying surface 46, the conveying belts 14, 16 are rotated and the second magnetic means 52, 54 are therefore also driven along the conveying paths 48, 50.

The second magnetic means 52, 54 may then come into contact with the external wall of the Petri dish 60 within a time-frame depending on the initial position of the second magnetic means 52, 54, relative to the Petri dish 60 when the conveying belts 14, 16 start rotating.

Thus, if the second magnetic means 52, 54 are situated away from the initial position of the Petri dish 60 on the conveying surface 46, then the second magnetic means 52, 54 come into contact with the external wall of the Petri dish 60 after a time-frame corresponding to the travel time for the second magnetic means 52, 54 on the conveying surface 46 to reach the Petri dish 60 which is immobile on the conveying surface 46.

Alternatively, if the second magnetic means 52, 54 are situated at a suitable distance from the initial position of the Petri dish on the conveying surface 46, then the second magnetic means 52, 54 come into contact with the external wall of the Petri dish 60 as soon as the conveying belts 14, 16 start rotating.

The conveying device 10 may be integrated within a conveying system comprising for example a control device (not visible), a detection device or an optical reading device such as described below.

The control device (not visible) makes it possible to control the operation of the driving means 18, 20, 22, 24. Thus, a user may decide to stop the movement of the conveying belts 14, 16 at any time according to the position of the second magnetic means 52, 54 and/or according to the position of the Petri dish 60 on the conveying surface 46 or before the Petri dish 60 arrives on the conveying surface 46, for example. The user therefore has the possibility of minimising the consequences pertaining to a high speed of the driving means 18, 20, 22, 24 such as the spilling of the contents of the Petri dish 60 or a rebound effect of the Petri dish 60 in the presence of an obstacle which impedes the movement of the Petri dish 60 on the conveying surface 46.

The detection device (not visible) such as an electro-optical sensor is electrically linked to the control device. Thus, the detection device may detect the position of the Petri dish 60 and/or of the second magnetic means 52, 54 at any time and regularly transmit information regarding the various positions to the control device. Thus, the control device may, with the aid of a suitable computer program, automatically manage the movements of the conveying belts 14, 16, second magnetic means 52, 54 and therefore control the conveying of the Petri dish 60.

The optical reading device makes it possible to read the content of the information medium 63 and transmit the content of the information medium to a data processor in order to process and/or analyse said information content.

The conveying device 10 also comprises various optional movement devices which are all suitable for use within the conveying device 10. The optional movement devices may be used separately or in combination within a conveying device 10. Thus, a conveying device 10 may comprise one or more optional movement devices. Alternatively, different optional movement devices may be arranged within different conveying devices, thus forming an assembly of devices. The present invention therefore makes it possible to obtain a large number of possible combinations to produce a conveying device 10 suitable for various restrictions such as the dimensions of the Petri dish 60, the space available for the conveying device, the location of the devices necessary for receiving the Petri dish for processing and/or analysing the Petri dish 60, or of the contents of the Petri dish 60.

Figure 5:
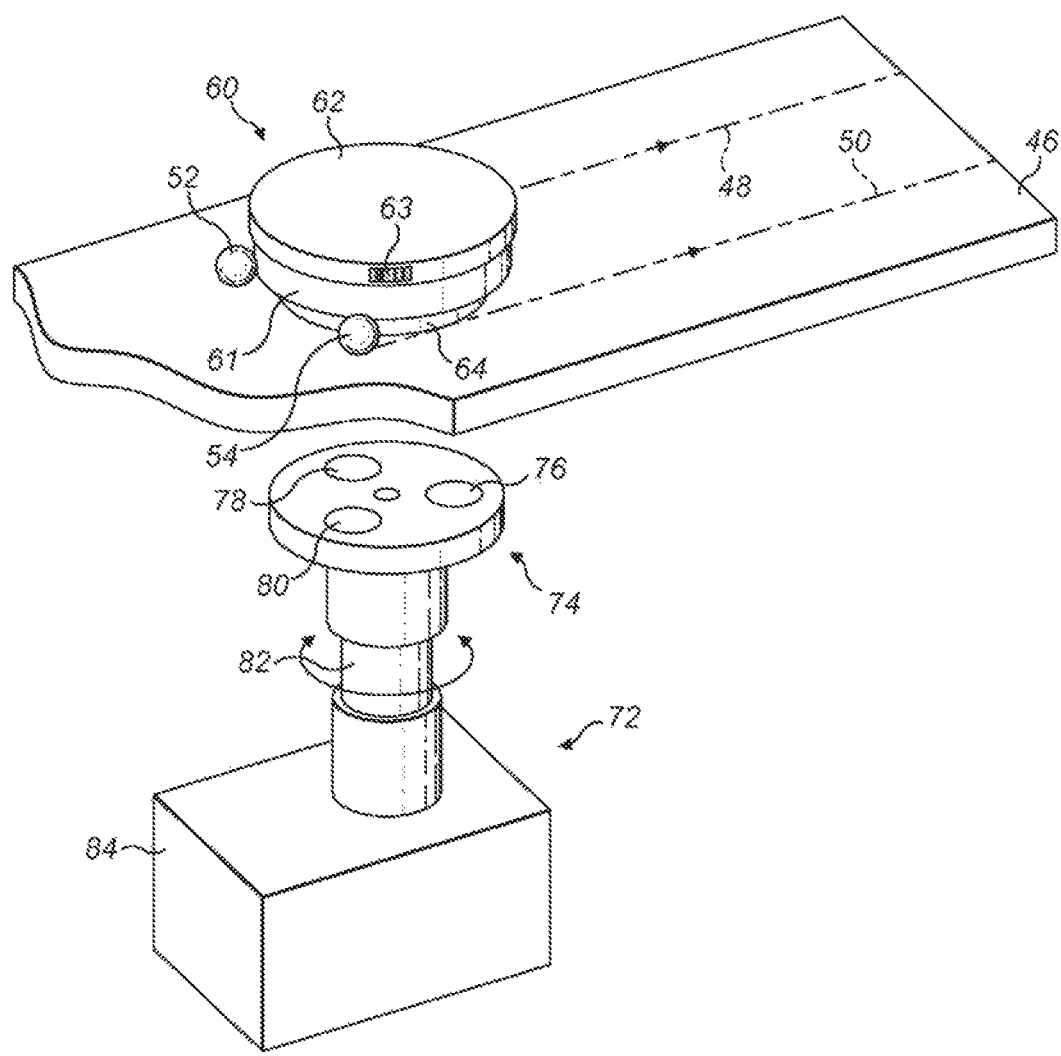
FIG. 5 shows a partial view of a conveying device according to FIG. 1, with a first movement device comprising a first magnetic movement means located on the conveying surface and a second magnetic movement means located below the conveying surface according to one embodiment of the invention.

Thus, the conveying device 10 may comprise a first movement device as shown in FIG. 5. The first movement device may be combined with the conveying device 10 in order to add a first optional conveying function. The first optional conveying function corresponds to a rotation of the Petri dish 60 about its vertical central axis without any translation of the Petri dish 60, by means of the contact surface of the Petri dish 60, i.e. the surface of the Petri dish 60 which is in contact with the conveying surface 46. This first function is hereafter named lower rotation.

Figure 6:
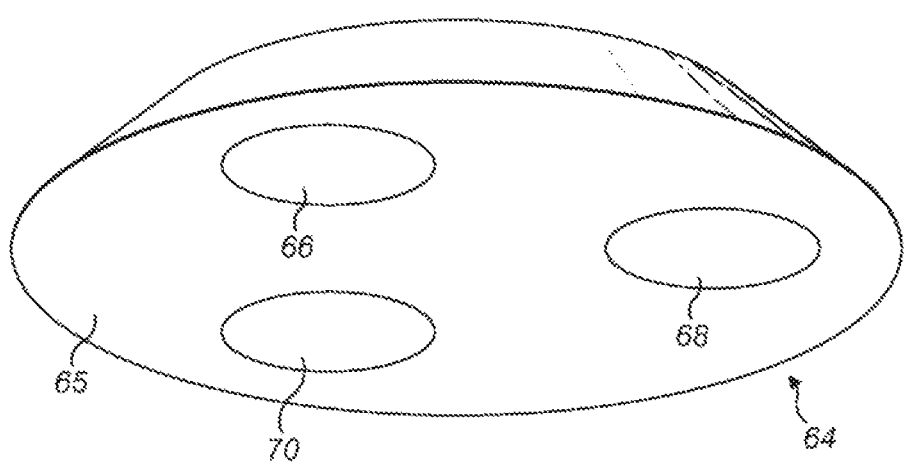
FIG. 6 shows in detail the first magnetic movement means of the first movement device according to FIG. 5 according to one embodiment of the invention.

As shown in FIG. 5, the first movement device comprises a first magnetic movement means 64 positioned removably on the conveying surface 46. The first magnetic movement means 64 is rotationally mobile and is made of a non-magnetic material such as plastic. As shown in detail in FIG. 6, the first magnetic movement means 64 comprises a first surface 65 in contact with the conveying surface 46 and smaller in size than the contact surface of the Petri dish 60. This first surface 65 comprises a plurality of ferromagnetic elements 66, 68, 70 in contact with the conveying surface 46.

According to a variant of this embodiment, the ferromagnetic elements 66, 68, 70 may not be directly in contact with the conveying surface 46. Indeed, the ferromagnetic elements 66, 68, 70 may be suitably integrated in order not to be visible on the surface 65. Alternatively, the ferromagnetic elements 66, 68, 70 may be replaced by permanent magnets. The first magnetic movement means 64 also comprises a second surface (not visible) which is not in contact with the conveying surface 46. The second surface comprises a receiving zone (not visible) in order to receive the Petri dish 60 moving on the conveying surface 46. Thus, to facilitate the insertion and the placement of the Petri dish 60 within the receiving zone, the first magnetic means 64 comprises suitable edges which are bevelled, for example, so that the Petri dish 60 may be inserted into the receiving zone without manual intervention by a user.

As shown in FIG. 5, the first movement device also comprises, below the conveying surface 46, a second magnetic movement means 72 comprising a rotationally mobile element 74 equipped with a plurality of permanent magnets 76, 78, 80. The rotationally mobile element 74 is linked at its centre via an axis of rotation 82, to a driving means 84 such as a stepper motor.

The permanent magnets 76 78, 80 and the ferromagnetic elements 66, 68, 70 are sized and positioned in order to cooperate, during the rotating of the rotationally mobile element 74. Thus, the first magnetic movement means 64 is also rotated on its own axis due to the magnetic attraction forces of the permanent magnets 76, 78, 80 on the ferromagnetic elements 68, 68, 70. In the presence of a Petri dish 60, within the receiving zone of the first magnetic movement means 64, when the first magnetic movement means 64 is rotated, the Petri dish 60 is also rotated. By means of the control device (not visible), a user may therefore decide to stop the rotation of the Petri dish 60 in order to place the Petri dish 60 in a fixed orientation notably in order to enable the information medium 63 to be read by means of the optical reading device (not visible). Alternatively the reading may be carried out during the rotation of the Petri dish 60.

Figure 7:
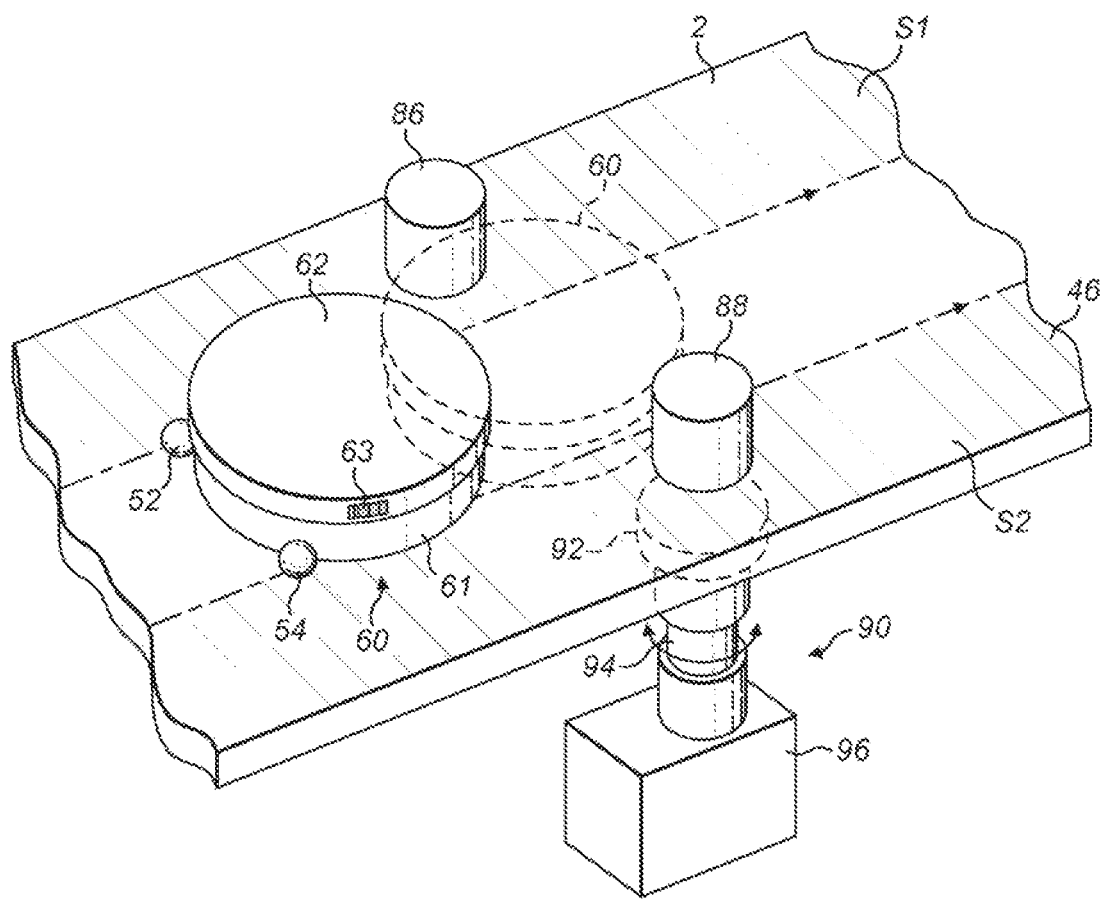
FIG. 7 shows a partial view of a conveying device according to FIG. 1, with a second movement device comprising a first and a second magnetic movement means located on the conveying surface, as well as a third and a fourth magnetic movement means located below the conveying surface according to one embodiment of the invention.

The conveying device 10 may also comprise a second movement device as shown in FIG. 7. The second movement device may be added to the conveying device 10 in order to add a second optional conveying function. The second optional conveying function corresponds to a rotation of the Petri dish 60 about its vertical central axis without any translation of the Petri dish 60, by means of the lateral surface of the Petri dish 60. This second function is called lateral rotation.

The second movement device comprises a first magnetic movement means 86 and a second magnetic movement means 88, which are rotationally mobile and located on the conveying surface 46, respectively inside the first internal surface S1 and the second internal surface S2, removably and symmetrically to the conveying paths 48, 50.

The first magnetic movement means 86 and the second magnetic movement means 88 each possess a contact surface (not visible) made of ferromagnetic material. The first magnetic movement means 86 and the second magnetic movement means 88 are arranged on the conveying surface 46 such that their respective contact surface is in contact with the conveying surface 46.

The second movement device also comprises a third magnetic movement means (not visible) and a fourth magnetic movement means 90 arranged below the conveying surface 46.

The third magnetic movement means (not visible) comprises a permanent magnet in order to create a fixed magnetic coupling with the first magnetic movement means 86, advantageously a weak magnetic coupling. Thus, the first magnetic movement means 86 may turn freely about its vertical central axis.

The fourth magnetic movement means 90 is sized and positioned in order to cooperate with the second magnetic movement means 88.

As shown in FIG. 7, the fourth magnetic movement means 90 comprises a rotationally mobile element 92 such as a permanent magnet. The fourth magnetic movement means 90 is linked at its centre, via an axis of rotation 94, to a driving means 96 such as a stepper motor. The fourth magnetic movement means 90 makes it possible to create a fixed magnetic coupling with the second magnetic movement means 88, advantageously a strong magnetic coupling. Thus, the second magnetic movement means 88 turns in a controlled manner about its vertical central axis.

Thus, in the presence of a strong magnetic coupling, when the second magnetic means 52, 54 are moved on a conveying path 48, 50 and come into contact with the Petri dish 60, said second magnetic means 52, 54 are not deflected from the conveying path 48, 50.

Alternatively, in the presence of a weak magnetic coupling, when the second magnetic means 52, 54 are moved on a corresponding conveying path 48, 50 and come into contact with the Petri dish 60, said second magnetic means 52, 54 are suitably deflected from the conveying path 48, 50. Thus, the second magnetic means 52, 54 may undergo a movement which corresponds to a separation according to a separation zone defined relative to the corresponding conveying path 48, 50, while preserving the effect of the magnetic coupling between the first magnetic means 26, 28 and the second magnetic means 52, 54. As indicated above, this separation makes it possible for the second magnetic means 52, 54 to remain in contact with the conveying path 48, 50 and to continue to drive the Petri dish 60 on the conveying surface 46.

The magnetic coupling may therefore be modulated by adapting the dimensions and the materials of the first magnetic means 26, 28 to the dimensions and the materials of the second magnetic means 52, 54. Thus, depending on the type of magnetic coupling, the second magnetic means 52, 54 have a fixed separation zone relative to the respective conveying paths 48, 50 when the conveying belts 14, 16 start rotating.

The first and second magnetic movement means 86, 88 are configured such that the first magnetic movement means 86 may turn freely about its vertical central axis in order to be freely rotated by a rotating Petri dish 60 when the latter is in contact, simultaneously, with said first magnetic movement means 86 and the second magnetic movement means 88 turning in a controlled manner about its vertical central axis. Indeed, the second magnetic movement means 88 rotates the Petri dish which transmits its rotational movement to the first magnetic movement means 86. The first magnetic movement means 86 is rotated by friction against the wall of the Petri dish 60, which itself is rotated by friction against the surface of the second magnetic movement means 88.

The second optional conveying function may be triggered by means of the control device (not visible). Thus, in the presence of a Petri dish 60, simultaneously in contact with the first and the second magnetic movement means 86, 88, a user may trigger the rotation of the fourth magnetic movement means 90 in order to generate the rotation of the assembly constituted by the second magnetic movement means 88, the Petri dish 60 and the first magnetic movement means 86.

Thus, when the Petri dish 60 is in the process of moving on the conveying surface 46 in the direction of the second magnetic movement device, the Petri dish 60 simultaneously comes into contact, at its lateral wall, with the first and the second magnetic movement means 86, 88. Since the second magnetic movement means 88 is actuated by a controlled rotational movement, the Petri dish 60 starts rotating about its vertical central axis by friction against the second magnetic movement means 88. Simultaneously, since the first magnetic movement means 86 is actuated by a free rotational movement about its vertical central axis, the rotating Petri dish 60 rotates the first magnetic movement means 86 by friction. The contact between the first magnetic movement means 86 and the lateral wall of the Petri dish 60 makes it possible to guarantee a stable position of the Petri dish 60 during rotation of the Petri dish 60.

Alternatively, the assembly formed by the first magnetic movement means 86 and the third magnetic movement means (not visible) and the assembly formed by the second magnetic movement means 88 and the fourth magnetic movement means 90 may occupy inverted positions on the conveying surface 46.

Figure 8:
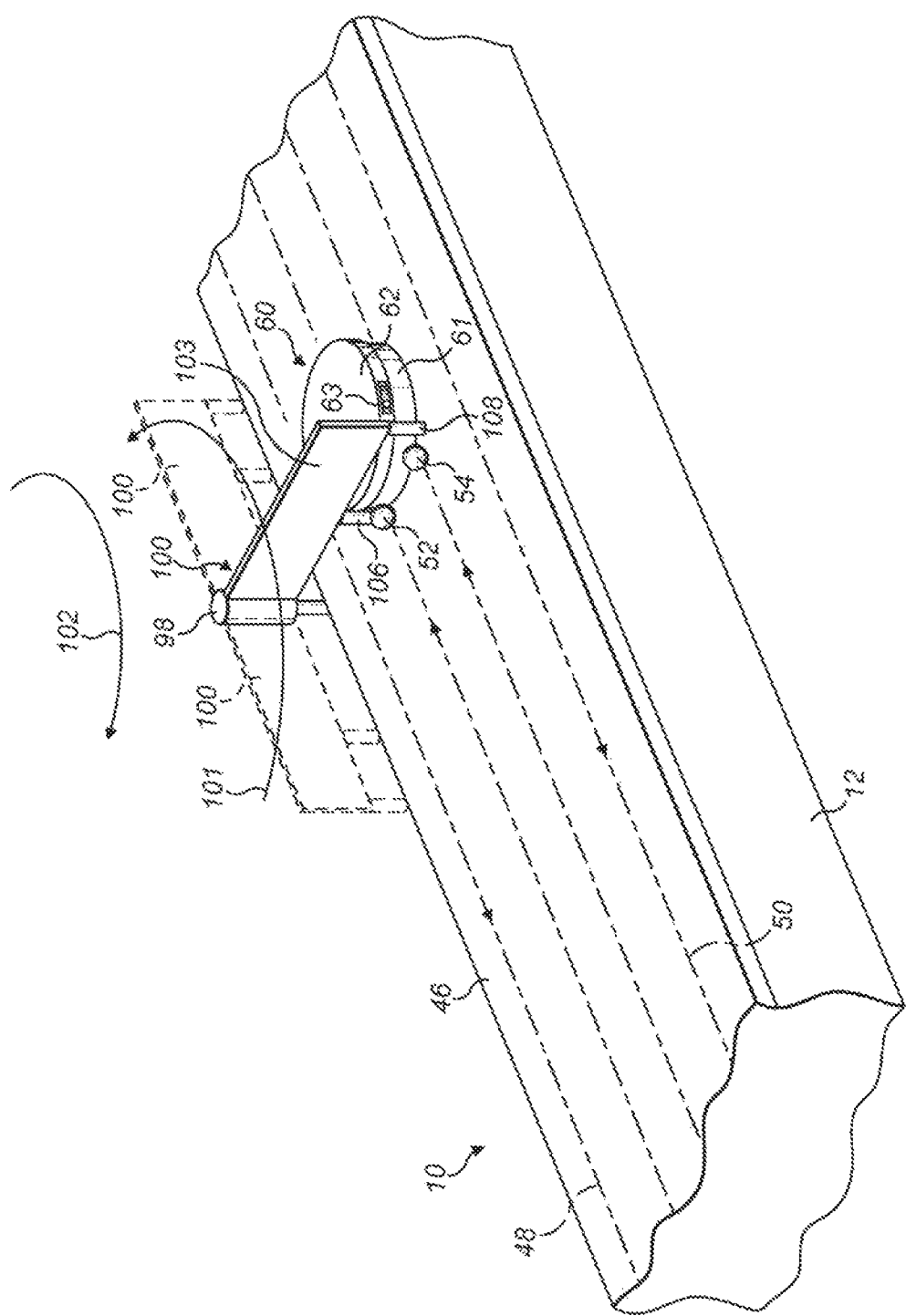
FIG. 8 shows a partial view of a conveying device according to FIG. 1 with a third movement device comprising a mechanical transfer means, in contact with the conveying surface according to one embodiment of the invention.

The conveying device 10 may also comprise a third movement device as shown in FIG. 8.

The third movement device comprises a mechanical transferring means arranged along the conveying surface 46. The third movement device may be added to the conveying device 10 in order to add a third optional conveying function. The third optional conveying function corresponds to an angular movement of the Petri dish 60 toward the exterior of the conveying surface 46 on which the Petri dish 60 is situated. This third function is called angular movement.

The mechanical transferring means comprises a rotating axial support 98 fixed close to the conveying surface 46 and made of a relatively rigid material such as a metallic material. The rotating axial support 98 may have a tubular shape and is equipped with a driving means (not visible) in order to rotate the rotating axial support 98 about its vertical central axis.

The rotating axial support 98 is equipped with a rotating arm 100 which is rotationally mobile when the rotating axial support 98 is rotated in a rotation direction indicated by the arrow 101 or in a reverse rotation direction indicated by the arrow 102. The rotating arm 100 possesses a contact surface 103 the dimensions of which are such that the length of the contact surface 103 is less than the width of the conveying surface 46. The rotating arm 100 may perform a movement, in the rotation direction 102, which moves in an arc such as a semi-circle from an initial position represented as a dotted line along the conveying surface 46 to a final position represented as a dotted line along the conveying surface 46.

The rotating arm 100 may also occupy an intermediate position represented by the rotating arm 100 as a solid line located above the conveying surface 46.

The rotating arm 100 is equipped with contact rods 106, 108 positioned so as to come into contact with the conveying surface 46 when the rotating arm 100 is in the intermediate position, without impeding the movement of the rotating arm 100 when said rotating arm 100 is in movement. The distance between the two contact rods 106, 108 is greater than the distance dmin and less than the distance dmax. The distance between the two contact rods is also suitable for enabling the contact rods 106, 108 to come into contact with the Petri dish 60 located on the conveying surface 46 when said Petri dish 60 is in movement.

With the aid of a control device (not visible), a user may control the operation of the mechanical transfer means. Thus, a user may use defined parameters in order to trigger the operation of the driving means of the rotating axial support 98 and move the rotating arm 100 from the initial position to the final position. The parameters may be associated with the identification of a fixed position of the Petri dish 60, for example. Thus, automatically or manually, when the Petri dish 60 is moving on the conveying surface, a user may operate the control device (not visible) to turn the rotating arm 100 once the Petri dish 60 passes a fixed position on the conveying surface 46. Thus, the contact rods 106 and 108 come into contact with the wall of the Petri dish 60 and move said Petri dish 60 in the trajectory of the rotating arm 100. The Petri dish 60 is therefore moved on the conveying surface 46 from the conveying path 48, 50 toward the exterior of the conveying surface 46.

The third movement device therefore makes it possible to extract the Petri dish 60 from the conveying surface 46 in order to transfer the Petri dish 60 to another conveying surface associated with another conveying device or even toward another destination such as a reject zone, for example.

According to a specific arrangement of one or more conveying devices, there are a large number of possibilities for moving the Petri dish 60 in a defined trajectory with the aid of the various movement devices.

Each type of movement device, i.e. the first, the second and the third, may all be arranged within the same conveying device or may each be arranged within a specific conveying device. There are a large number of possible combinations in order to combine the various types of movement device within one or more conveying devices.

Furthermore, the conveying devices may be juxtaposed according to a large number of possibilities, either aligned on the same horizontal plane in order to obtain an integrated conveying surface encompassing all of the conveying surfaces of the different conveying surfaces, or in different horizontal planes. According to this last embodiment, additional ramps may be provided to enable the Petri dish 60 to move from a conveying surface of a first conveying device belonging to a first horizontal plane to a conveying surface of a second conveying device belonging to a second horizontal plane for example.

Figure 9:
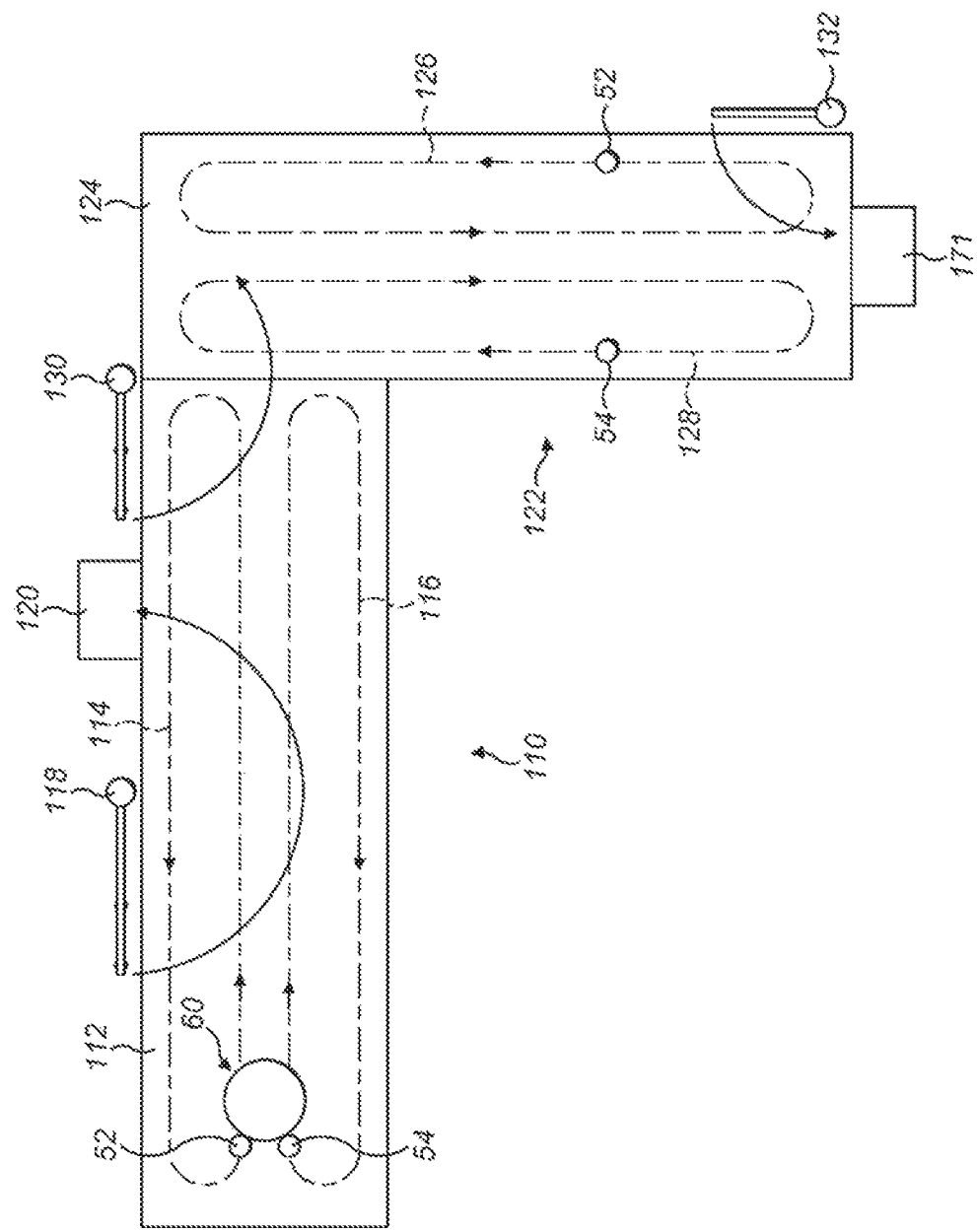
FIG. 9 shows a combination of two conveying devices, each comprising two conveying belts, and a plurality of third movement devices according to FIG. 8 according to one embodiment of the invention.
Figure 10:
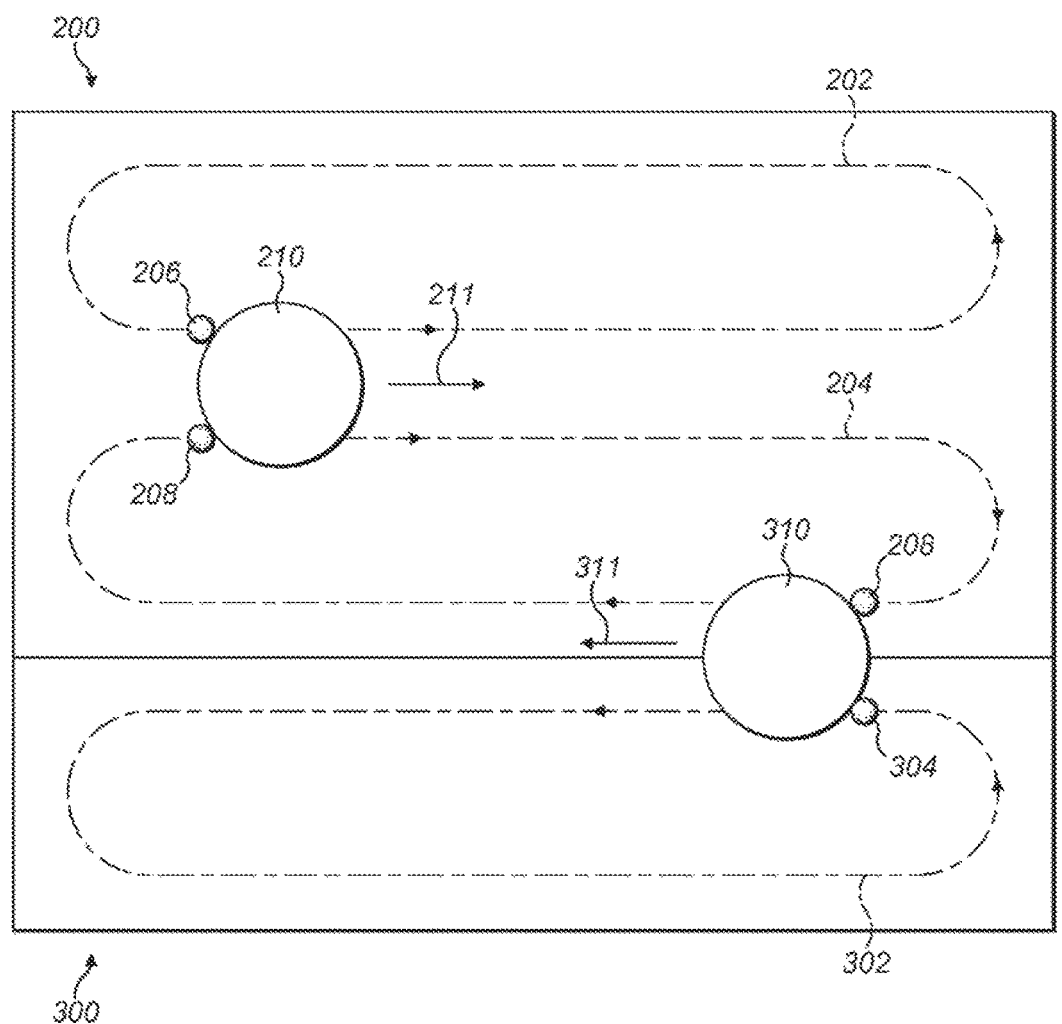
FIG. 10 shows a combination of a first conveying device comprising two conveying belts with a second conveying device comprising a conveying belt according to one embodiment of the invention.

Examples of juxtaposition of conveying devices are shown in FIGS. 9 and 10. Two conveying devices are juxtaposed on the same horizontal plane.

As shown in FIG. 9, the first conveying device 110 comprises a conveying surface 112 comprising two conveying paths 114, 116 and two second magnetic means 52, 54 in order to convey a Petri dish 60. The first conveying device 110 also comprises a movement device 118 for an angular movement of the Petri dish 60 in order to move the latter to an element 120 such as a storing zone and thus to collect the Petri dish 60 after conveying on the conveying surface 112.

As shown in FIG. 9, a second conveying device 122 is juxtaposed with the first conveying device 110, on the same horizontal plane as the first conveying device 110.

The second conveying device 122 comprises a conveying surface 124 comprising two conveying paths 126, 128. A movement device 130 such as a mechanical transfer means for angular movement of the Petri dish 60 is positioned at the interface between the first and second conveying devices 110, 122. The movement device 130 makes it possible to move the Petri dish 60 from the conveying surface 112 of the first conveying device 110 to the conveying surface 124 of the second conveying device 122. Thus, when the Petri dish 60 arrives close to the movement device 130, the latter is triggered by means of the control device in order to transfer the Petri dish 60 from the conveying surface 112 to the conveying surface 124 on the conveying paths 126, 128.

The second conveying device 122 is also equipped with a second movement device 132 for angular movement of the Petri dish 60 in order to collect the various objects such as the Petri dish 60, after the conveying of these objects on the conveying surface 124. Each conveying device 110, 122 comprises a control device (not visible). Alternatively, one single control device may be used for all of the conveying devices.

Another example of juxtaposition of conveying devices is shown in FIG. 10. Two conveying devices 200 and 300 are juxtaposed on the same horizontal plane.

The conveying device 200 comprises a first conveying belt 202 and a second conveying belt 204. The conveying device 200 also comprises a first magnetic driving device associated with the first conveying belt 202. The first magnetic driving device comprises a first magnetic means (not visible) and a second magnetic means 206. The conveying device also comprises a second magnetic driving device associated with the second conveying belt 204. The second magnetic driving device comprises two first magnetic means (not visible) and two second magnetic means 208. The conveying device 200 makes it possible to convey an object 210 from an initial position to a final position in the direction indicated by the arrow 211 shown in FIG. 10. The object 210 is preferably a Petri dish.

The conveying device 300 comprises a conveying belt 302. The conveying device 300 also comprises a magnetic driving device associated with the conveying belt 302. The magnetic driving device comprises a first magnetic means (not visible) and a second magnetic means 304.

The conveying devices 200 and 300 are juxtaposed such that an object 310, such as a Petri dish, may be conveyed by means of magnetic driving means associated with the conveying belts 204, 302 respectively of the first conveying device 200 and of the second conveying device 300.

Thus, when the object 210 reaches its final position on the conveying device 200, the object 310 may be placed in the initial position, between the two conveying belts 204 and 302 in order to be conveyed to its final position.

Alternatively, the conveying device 300 may also comprise a second conveying belt to make it possible to convey a third object in the direction indicated by arrow 211, in a similar manner to the conveying performed by means of conveying device 200.

The possibilities for combining conveying devices may thus vary depending on the structural restrictions of the environment within which an object, in particular a Petri dish, needs to be conveyed.

Alternative embodiments of conveying devices comprising a single conveying belt are described below.

Figure 11:
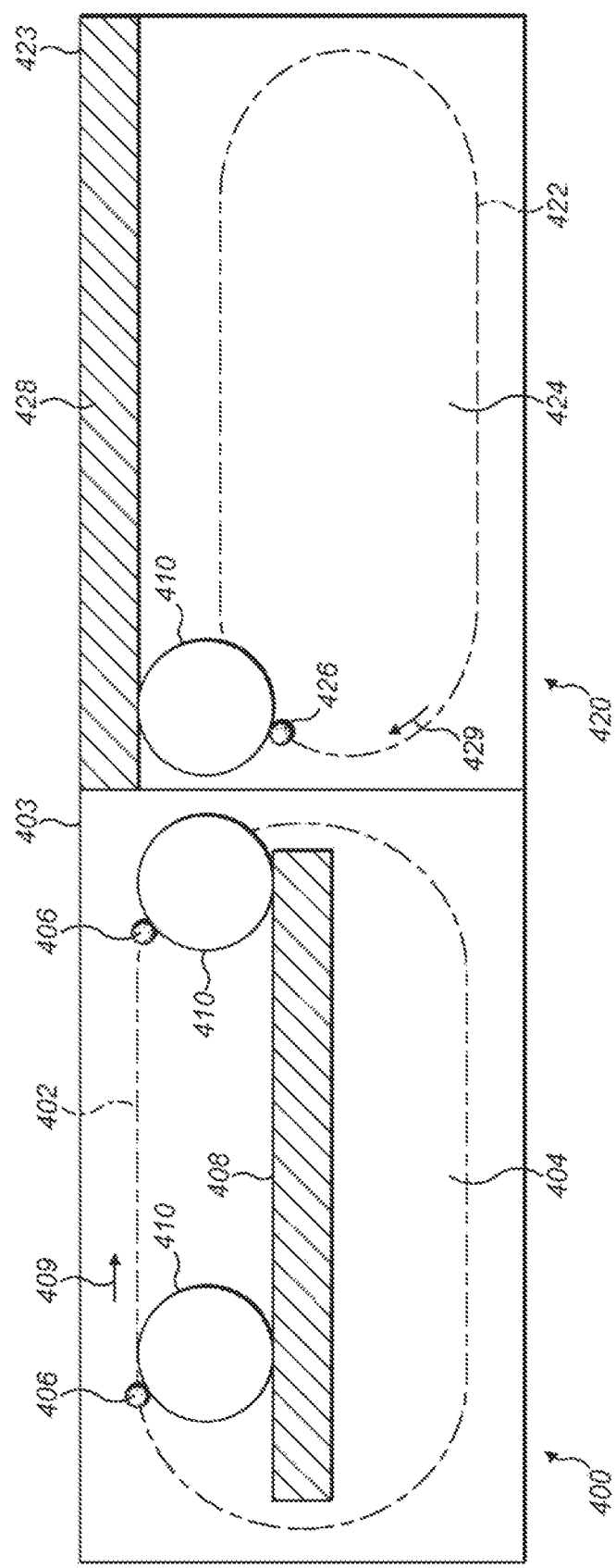
FIG. 11 shows a combination of two conveying devices, each comprising a conveying belt, a magnetic driving device and a contact device comprising a guiding device such as a central immobile support according to one embodiment of the invention.

Thus, FIG. 11 shows a conveying device 400 comprising a conveying belt 402 which delimits, on a conveying surface 403, an interior surface 404. The conveying device 400 also comprises a magnetic driving device comprising a first magnetic means (not visible) and a second magnetic means 406. The conveying device 400 also comprises a contact device comprising a guiding device 408 positioned in the centre of the interior surface 404 such as an immobile central support which is made of plastic, for example. The guiding device 408 is removable on the conveying surface 403 and comprises two rectilinear longitudinal surfaces parallel to the direction of the conveying belt 402 indicated by the arrow 409. The conveying device 400 makes it possible to convey an object 410, preferably a Petri dish. Thus, the object 410 is conveyed in the direction of the arrow 409 from an initial position to a final position. The distance between the conveying belt 402 and the guiding device 408 is fixed such that the second magnetic means 406 may circumvent the guiding device 408 when the object 410 arrives in a final position close to the end of the guiding device 408.

FIG. 11 also shows a conveying device 420 juxtaposed with the conveying device 400. The conveying device 420 comprises a conveying belt 422 which delimits, on a conveying surface 423, an interior surface 424. The conveying device 420 also comprises a magnetic driving device comprising a first magnetic means (not visible) and a second magnetic means 426. The conveying device 420 also comprises a contact device made up of a guiding device 428 positioned outside of the interior surface 424. The guiding device 428 is removable on the conveying surface 423 and comprises two rectilinear longitudinal surfaces parallel to the direction of the conveying belt 422 indicated by the arrow 429. The conveying device 420 makes it possible to convey the object 410 starting from the conveying device 400. Thus, the object 410 is conveyed in the direction of the arrow 429 from an initial position to a final position. The distance between the conveying belt 422 and the guiding device 428 is fixed such that, when the object 410 arrives in a final position close to the end of the guiding device 428, the second magnetic means 426 pushes the object 410 toward the guiding device 428.

Thus, when the object 410 reaches a final position close to the end of the guiding device 408, the movement of the object 410 is restricted by the second magnetic means 406 and the guiding device 408. Thus, the object 410 is moved in a guided manner toward the conveying device 420 and finds its movement once again restricted by the second magnetic driving device 426 and the guiding device 428. The object 410 is thus moved on the conveying surface 422 of the conveying device 420.

A similar combination of conveying devices could be envisaged for conveying devices comprising two conveying belts.

Figure 12:
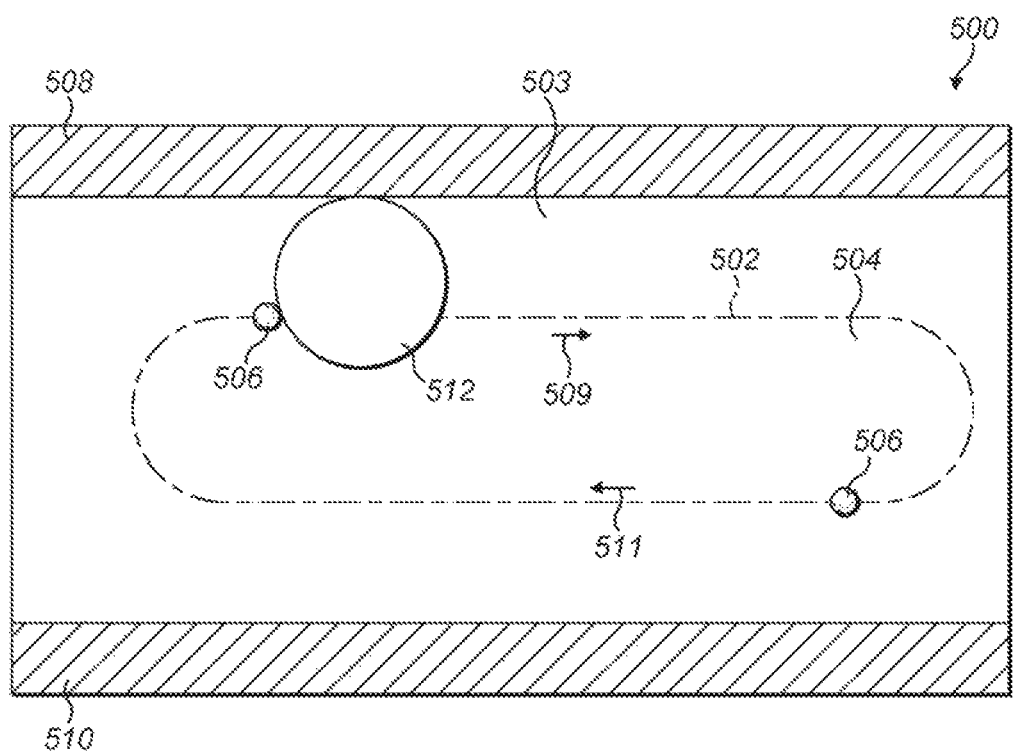
FIG. 12 shows a conveying device comprising a conveying belt, a magnetic driving device and a contact device such as a guiding device, such as two immobile side supports according to one embodiment of the invention.

Alternatively, FIG. 12 shows a conveying device 500 comprising a conveying belt 502 which delimits, on a conveying surface 503, an interior surface 504. The conveying device 500 also comprises a magnetic driving device comprising a first magnetic means (not visible) and a second magnetic means 506. The conveying device 500 also comprises two contact devices such as two guiding devices 508 and 510 positioned on the conveying surface 503, outside of the interior surface 504. The guiding devices 508, 510 such as two immobile lateral supports made of a plastic material, for example, are removable on the conveying surface 503. The guiding devices 508, 510 each comprise a rectilinear longitudinal surface parallel to the direction of the conveying belt 502 indicated by the arrow 509. The conveying device 500 makes it possible to convey an object 512, preferably a Petri dish. The distance between the conveying belt 502 and each guiding device 508, 510 is fixed such that the object 512 is simultaneously in contact with the second magnetic means 506 and the guiding device 508 on the one hand and with the second magnetic means 506 and the guiding device 510 on the other hand. Thus, the object is conveyed in the direction of the arrow 509 from an initial position to a final position on the one hand and in the direction of the arrow 511 on the other hand.

The conveying device may comprise at least one magnetic driving device associated with a contact device comprising either another magnetic driving device or at least one guiding device. The use of two magnetic driving devices enables optimum movement of the Petri dish compared to using a magnetic driving device associated with a guiding device. Indeed, in the presence of two magnetic driving devices, the overall movement force applied to the Petri dish 60 is greater than the single movement force applied to the Petri dish 60 in the presence of a single magnetic driving device associated with a guiding device.

According to the present invention, the conveying device may be used alone or in combination with other conveying devices.

Each conveying device may comprise at least one belt and optionally one or more movement devices.

The invention claimed is:

1. A device for conveying an object in order to move said object from an initial position to a final position, on a conveying surface, said conveying device comprising:
  at least one conveying belt rotationally mobile with the aid of corresponding driving means and which is located under the conveying surface, said at least one conveying belt making it possible to define a first conveying path on the conveying surface;
  a magnetic driving device comprising:
    at least one first magnetic means integral with said at least one conveying belt and displaced with said conveying belt below the conveying surface; and
    at least one second magnetic means positioned on the conveying surface and suitable for moving on said conveying surface, driven by said at least one first magnetic means through the conveying surface;
  a contact device suitable for applying a contact force onto an external wall of the object,
  wherein, when said at least one conveying belt is moving in the presence of an object on the conveying surface, the second magnetic means is moved on the conveying surface, along the first conveying path, driven by the first magnetic means, and wherein the second magnetic means pushes onto the external wall of the object, and
  wherein the contact device simultaneously applies at least one contact force onto the external wall of the object to enable guided movement of said object on the conveying surface.

2. The conveying device according to claim 1, wherein the contact device comprises a second magnetic driving device comprising:
  at least one first magnetic means integral with at least one second conveying belt and moving with said at least one second conveying belt below the conveying surface; and
  at least one second magnetic means positioned on the conveying surface and suitable for moving on said conveying surface driven by said at least one first magnetic means through the conveying surface.

3. The conveying device according to claim 2, wherein the at least one first magnetic means of the second magnetic driving device comprises a permanently magnetized magnetic means.

4. The conveying device according to claim 2, wherein the at least one second magnetic means of the second magnetic driving device comprises a ferromagnetic means.

5. The conveying device according to claim 1, wherein the contact device comprises a guiding device positioned on the conveying surface.

6. The conveying device according to claim 5, further comprising a conveying belt,
  wherein the guiding device comprises a central support which is immobile on the conveying surface.

7. The conveying device according to claim 1, further comprising a first movement device including a first magnetic movement means located removably between the first conveying path and a second conveying path on the conveying surface and suitable for cooperating with a second magnetic movement means located below the conveying surface to rotate the first magnetic movement means.

8. The conveying device according to claim 7, further comprising a second movement device including a first magnetic movement means located removably inside the first conveying path on the conveying surface and suitable for cooperating with a third magnetic movement means located below the conveying surface to enable a free rotation of the first magnetic movement means.

9. The conveying device according to claim 8, wherein the second movement device further comprises a second magnetic movement means located removably inside the second conveying path on the conveying surface and suitable for cooperating with a fourth magnetic movement means located below the conveying surface to rotate the second magnetic movement means.

10. The conveying device according to claim 1, further comprising a third movement device comprising a rotating arm located on or above the conveying surface and actuated by an angular movement of a fixed angle value for moving the object on the conveying surface.

11. The conveying device according to claim 1, wherein the at least one first magnetic means comprises a permanently magnetized magnetic means.

12. The conveying device according to claim 1, wherein the at least one second magnetic means comprises a ferromagnetic means.

13. A conveying system comprising at least one conveying device, said at least one conveying device comprising:
- at least one conveying belt rotationally mobile with the aid of corresponding driving means and which is located under a conveying surface, said at least one conveying belt making it possible to define a first conveying path on the conveying surface;
- a magnetic driving device comprising:
  - at least one first magnetic means integral with said at least one conveying belt and displaced with said conveying belt below the conveying surface; and
  - at least one second magnetic means positioned on the conveying surface and suitable for moving on said conveying surface, driven by said at least one first magnetic means through the conveying surface;
- a contact device suitable for applying a contact force onto an external wall of the object,
- wherein, when said at least one conveying belt is moving in the presence of an object on the conveying surface, the second magnetic means is moved on the conveying surface, along the first conveying path, driven by the first magnetic means, and wherein the second magnetic means pushes onto the external wall of the object, and
- wherein the contact device simultaneously applies at least one contact force onto the external wall of the object to enable guided movement of said object on the conveying surface.

14. The conveying system according to claim 13, wherein the at least one conveying device comprises a detection device for detecting the position of the object on the conveying surface.

15. The conveying system according to claim 14, comprising a control device configured to control the movement of said at least one conveying belt.

16. The conveying system according to claim 15, further comprising:
- a first movement device including a first magnetic movement means located removably between the first conveying path and a second conveying path on the conveying surface and suitable for cooperating with a second magnetic movement means located below the conveying surface to rotate the first magnetic movement means;
- a second movement device including a first magnetic movement means located removably inside the first conveying path on the conveying surface and suitable for cooperating with a third magnetic movement means located below the conveying surface to enable a free rotation of the first magnetic movement means; and
- a third movement device comprising a rotating arm located on or above the conveying surface and actuated by an angular movement of a fixed angle value for moving the object on the conveying surface,
- wherein said control device enables control of the triggering of one or more of the first movement device, the second movement device, and the third movement device as a function of the detected position of the object on the conveying surface.

17. The conveying system of claim 14, wherein the detection device comprises an electro-optical sensor.

18. The conveying system according to claim 13, further comprising an optical reading device for reading the content of an information medium located on the object.

19. A conveying method for moving an object on a conveying surface from an initial position to a final position, at least one first magnetic means being arranged below the conveying surface, said at least one first magnetic means being integral with at least one conveying belt, a second magnetic means being arranged on the conveying surface and suitable for cooperating with the first magnetic means through the conveying surface and for applying a movement force onto the external wall of the object, said conveying method comprising:
- rotating at least one conveying belt with the aid of driving means in order to enable movement of the first magnetic means;
- enabling guided movement of said second magnetic means along a corresponding conveying path on the conveying system via cooperation of the first magnetic means and the second magnetic means; and
- simultaneously pushing on the external wall of the object with the magnetic means and applying at least one contact force onto the external wall of the object by a contact device to enable guided movement of the object on the conveying surface.

* * * * *